's Patent [19]

Keim

[11] 4,361,651
[45] Nov. 30, 1982

[54] PROCESS FOR MAKING FERMENTABLE SUGARS AND HIGH-PROTEIN PRODUCTS

[76] Inventor: Carroll R. Keim, 50 Glenbrook Rd., Stamford, Conn. 06902

[21] Appl. No.: 170,033

[22] Filed: Jul. 18, 1980

[51] Int. Cl.³ .......................... C12P 7/06; C12P 19/20
[52] U.S. Cl. ........................................ 435/161; 435/96
[58] Field of Search ............... 435/161, 162, 163, 164, 435/165, 93, 813, 96, 97

[56] References Cited

U.S. PATENT DOCUMENTS

| | | | |
|---|---|---|---|
| 3,236,740 | 5/1961 | Smith et al. | 435/161 |
| 4,069,103 | 1/1978 | Müller | 435/99 |
| 4,242,454 | 12/1980 | Muller et al. | 435/162 |
| 4,242,455 | 12/1980 | Muller et al. | 435/162 |
| 4,243,750 | 1/1981 | Muller et al. | 435/162 |
| 4,255,518 | 3/1981 | Muller et al. | 435/161 |

OTHER PUBLICATIONS

Whistler et al., Starch: Chemistry and Technology, vol. II, p. 30, 1967.

Primary Examiner—Raymond N. Jones
Assistant Examiner—John E. Tarcza
Attorney, Agent, or Firm—Albert F. Kronman

[57] ABSTRACT

Disclosed is a dry or wet milling process for making fermentable sugars and high-protein products from starch bearing material, characterized by saccharification of the starch followed by recovery of fiber and other non-protein materials and of destarched protein as separate products, leaving a sugar solution that is essentially free of insoluble materials. The sugars are fermented to ethanol and carbon dioxide by the action of added yeast. After fermentation, the yeast is recovered for use in fermenting additional quantities of sugars supplied either for batch or continuous processing. The alcohol is then removed leaving a dilute solution of unfermentable soluble materials, and this liquid, in whole or in part, is recycled to preceding steps in the process.

13 Claims, 4 Drawing Figures

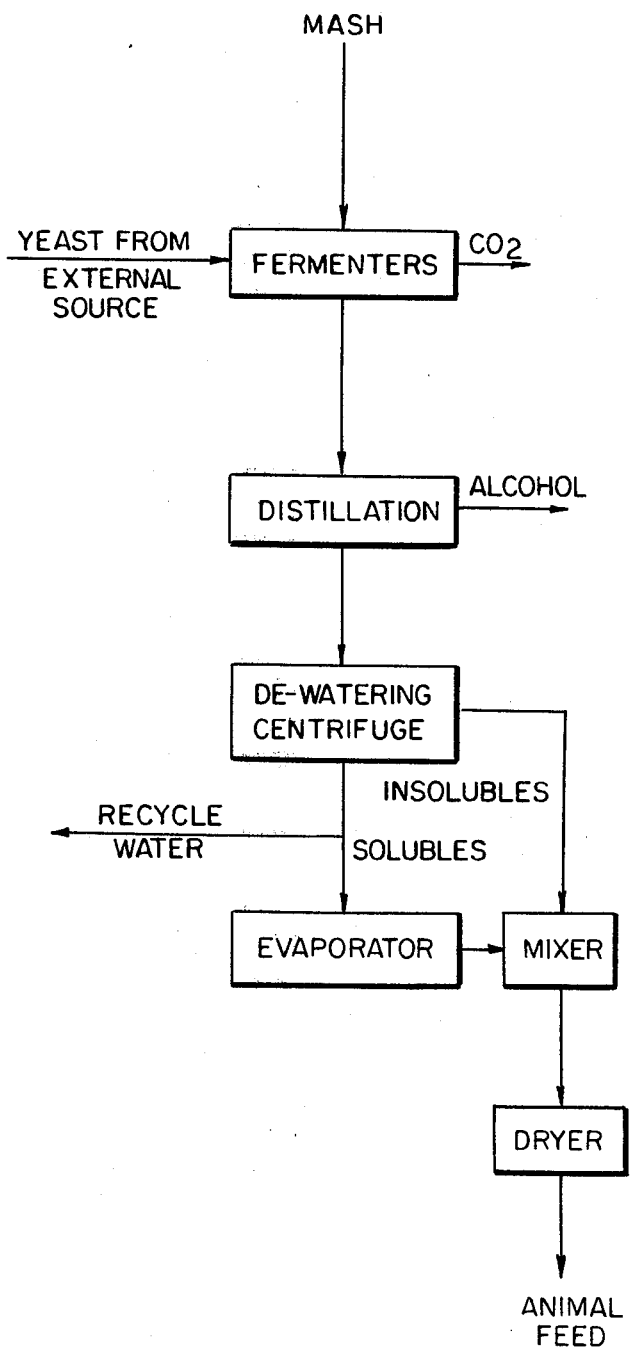
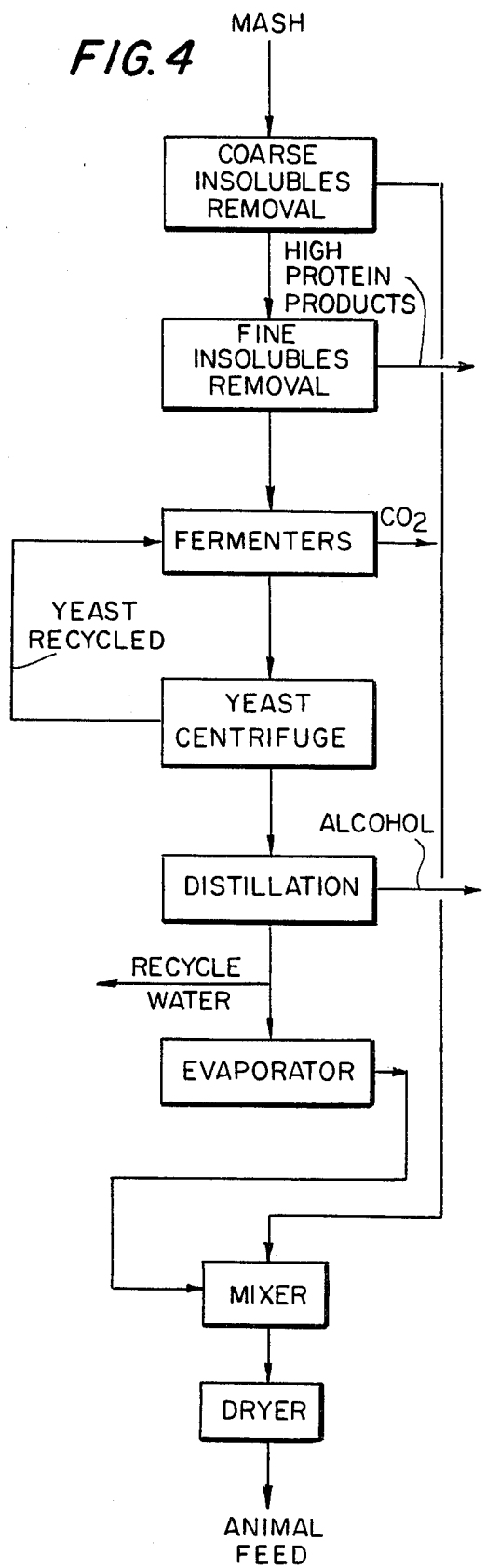
FIG.3
FIG.4

PROCESS FOR MAKING FERMENTABLE SUGARS AND HIGH-PROTEIN PRODUCTS

BACKGROUND OF THE INVENTION

Materials which contain starch and protein, often accompanied by other soluble and insoluble substances, are commercially processed to separate these materials into various fractions, which may also be further processed, if desired. The weight of each fraction, its composition and the total percentage of material recovered depends both upon the composition of the raw material and on the exact processing steps to which it is subjected.

In commercial processing, it is desired to maximize the total value of all the fractions recovered, as long as the increased value is greater than any increased costs of processing. In general, the value of a fraction is greater as its purity is increased, and the total value is greater with increased recovery of the more valuable fractions.

The art to which this invention relates has been very active through the years, as evidenced by the following patents:

U.S. Pat. No. 2,698,826 refers to a process wherein a starchy material is transformed into a magma containing solubles and unconverted starch which is centrifuged to provide an overflow containing the solubles and an underflow containing the starch. A fresh water wash is introduced into the centrifuge zone.

In U.S. Pat. No. 3,236,740 there is disclosed a process for producing alcohol which entails degerminating corn to form a germ fraction and a degerminated starchy fraction; extracting the germ fraction for its germ oil; adding some of the extract to the degerminated fraction; cooking the combined fractions; neutralizing the cooked material, cooling the cooked mash to saccharifying temperature; saccharifying the cooled mash cooling to fermenting temperature; fermenting and recovering the alcohol.

U.S. Pat. No. 3,236,740 discloses a process wherein, instead of milling the fiber after germ removal and separation of the "grit starch", the fiber and its associated starch and protein are put through an alcohol-making procedure. In this process, yeast is not recycled and starch is lost to fermentation with the germ and gluten coming from the primary separator.

U.S. Pat. Nos. 2,230,318 and 2,063,223 describe the re-use of yeast to increase alcohol yeilds but only in reference to molasses, which is clarified before fermentation.

Distilleries typically produce grain alcohol by converting the starch in grain to sugar, fermenting the sugar to alcohol, recovering the alcohol by distillation, and recovering the remaining materials by removing the water. This residual material is sold as animal feed and has much less value than the alcohol. The total value of production is increased by maximizing the recovery of starch as alcohol rather than allowing it to go to the feed fraction which has lower value. Furthermore, the value of the feed is improved through effective increase of its protein content when the starch is kept out of it.

Accordingly, it is an object of the present invention to provide a process for producing alcohol from corn, starchy roots, legumes and grain which yields a higher percentage of alcohol than prior art processes.

Another object of the present invention is to provide a process for producing by-products with a much higher economic value than prior art processes.

A further object of the present invention is to provide a process for producing alcohol which uses less water and energy than prior known processes.

Still another object of the present invention is to produce a new and valuable product, destarched corn gluten.

SUMMARY

The present invention is concerned with processes for maximizing the cumulative total value of the products made from starch-bearing materials that contain insoluble proteinaceous material, with or without containing other insoluble and/or soluble substances, by recovering the starch in high yields in the form of soluble carbohydrates or as fermentation products and by recovering an unusually high percentage of the insoluble protein present in a highly purified form.

Suitable raw materials include starchy roots, legumes, and grains, but the preferred materials are cereal grains or fractions of cereal grains which have been prepared by wet or dry separation methods.

One of the most advantageous uses of the processes is in the manufacture of volatile products of carbohydrate fermentation, especially of ethyl alcohol (also known as ethanol, alcohol, grain spirits, etc.)

This novel process for producing alcohol from corn, compared with regular distillery practice:
  produces higher alcohol yields
  produces by-products with much higher value
  uses less fresh water and thus consumes less energy for evaporation and drying,
and compared with previously used combinations of wet-milling and alcohol processes:
  uses less equipment
  recovers a substantially greater amount of starch as alcohol
  loses less protein to Corn Gluten Feed
  produces a new and valuable product-Destarched Corn Gluten.

The corn is steeped for a length of time in warm water that has been acidified with $SO_2$, at about 50° in tanks through which the water flows successively, as is standard practice in the corn wet-milling industry. The process differs from the standard procedure (where starch is sought as the prime product) in that steeping is carried out for a shorter period of time, only long enough to toughen the hull and germ sufficiently to make clean germ removal possible in the next step. Because of the shorter period of steeping, there is less solubilization of starch and protein, and therefore, a lower yield of steepwater solids than otherwise. The carbohydrates and proteins that would otherwise be solubilized are now available for recovery as alcohol and gluten respectively. Light steepwater exiting the system is kept preferably high in solids to reduce the amount of water to evaporate in the following evaporator. This is accomplished by reducing the amount of fresh water supplied to the whole system.

BRIEF DESCRIPTION OF THE DRAWINGS

In the accompanying diagramatic drawings forming part hereof similar elements have been given the same reference numeral, in which drawings;

FIG. 3 is a flow sheet illustrating the prior art dry milling process; and

FIG. 4 is a flow sheet showing a preferred dry milling embodiment according to the instant invention.

DETAILED DESCRIPTION

Figure 1:
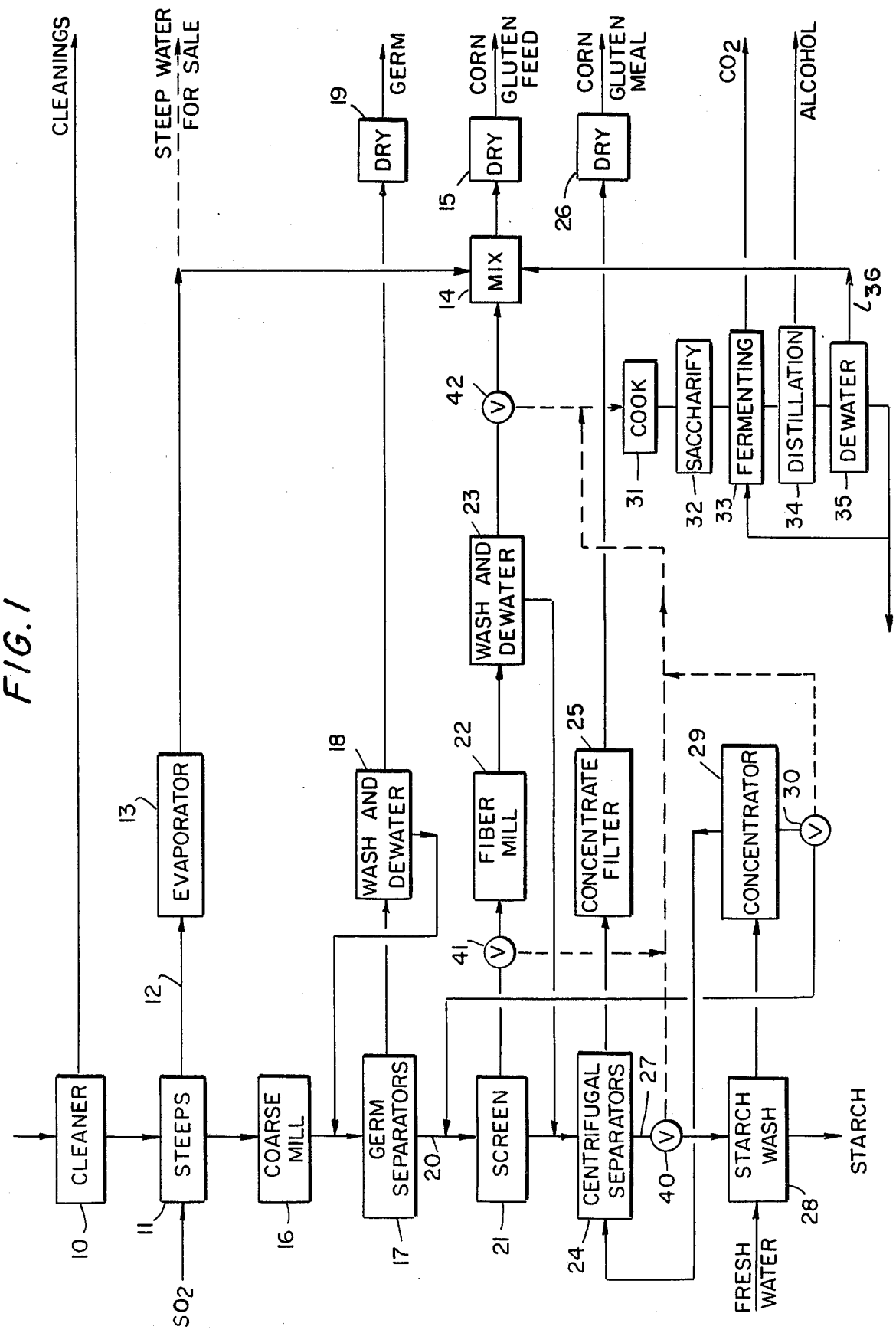
FIG. 1 is a flow diagram showing the prior art process and modifications in accordance with this invention.

In the traditional distillery operation, dry grain is ground by roller or hammer mills, cooked with water, treated with malt, acid or enzyme to convert starch into sugars, followed by fermentation with yeast, distillation of the alcohol and recovery of the unfermented materials by evaporation and drying of the water remaining after alcohol removal. Part of the sugars are consumed in growing yeast both in the fermenting step and in a propagation step carried on outside of the process. This diversion of sugar causes a corresponding reduction in yield of alcohol. Large amounts of fresh water are used in the cooking and fermentation steps, with correspondingly large amounts to be evaporated and dried in recovering the by-product.

The cost of alcohol produced by this method is inherently high because of low alcohol yields, low value of the single by-product, and high steam consumption for evaporating and drying the large amounts of water.

Because of the high costs entailed, the traditional distillery process has been largely supplanted, in the United State at least, wherever Grain Neutral Spirits for beverage purposes, or industrial alcohol for solvent or chemical intermediate purposes is required. Industrial grades have been mostly made by the hydration of ethylene, and the Grain Neutral Spirits are now made almost entirely in combination with processes originally designed to recover other valuable products from grain.

The most important of these is the corn wet-milling process which has been developed over a period of more than one hundred years as a means of obtaining in as pure a state as possible, the starch that is present in the kernels of corn. (See FIG. 1).

This process is reasonably standard, but may be practiced with variations in details according to local circumstances. In addition to starch, it recovers other components of the kernel, such as protein, oil, fiber, and ash in the form of more or less refined by-products. The general process may also be used in the recovery of starch and by-products from other grains such as wheat, sorghum (milo), barley, etc.

In the wet-milling process as usually practiced with corn, (see FIG. 1), shelled grain is cleaned in stage 10, to remove gross impurities, tramp metal, small particles and dust. In steeping stage 11, the cleaned kernels are steeped in water containing soluble ingredients of corn and a quantity of sulfur dioxide, for a period of up to 40 hours or more at a temperature of approximately 50° C. (122° F.). The sulfur dioxide water permeates into the kernel; it toughens the outer hull, toughens the corn gear, which contains most of the oil, and softens protein material that holds the germ and hull to the inner part of the kernel. The inner part of the kernel consists of a matrix of protein enclosing granules of starch, and the steeping process also serves to soften this protein network, to facilitate recovery of the maximum amount of starch.

During the stepping process, the water used for soaking is moved counter-currently to the corn, and is removed in the form of "light steepwater" 12 which contains protein, ash, cabohydrate, lactic acid, etc. at a dry substance concentration of some 3 to 10%. The light steepwater is subsequently concentrated by an evaporator 13 for sale as is, or to be combined in mixer 14 with fiber and other materials and dried 15 for use as an ingredient (corn gluten feed) in animal feed formulas.

After steeping, the kernels are drained of excess water and are coarsely milled at 16 to free the toughened germ from the rest of the kernel. Because the germ contains a large amount of oil, it is lighter than the other components of the kernel so it can be separated by gravimetric methods from the remaining magma by settling in germ separator 17 or by hydroclones, as practiced by those skilled in the art. Two stages of milling and separation are usually used; the germ is countercurrently washed free of adhering materials, dewatered as indicated at 18, and dried at 19. Valuable corn oil is removed from it either by expelling or solvent extraction (not shown).

The remaining magma 20 consists of fiber, starch, and protein (gluten); some of the starch and gluten are freely suspended in the water but a large amount also remains attached to the cellulosic fiber of the hull. The loose particles are screened out at 21 and advanced in the process, while the fiber is treated to free the adhering protein and starch. This is accomplished by a fiber mill 22, followed by a series of washing steps and dewatering 23 suspending the fiber in water, screening it, resuspending it, etc., with the water moving countercurrently to the fiber. The milled and washed fiber is then mixed in mixer 14 and other materials, and dried at 15 to produce corn gluten feed. The protein and starch which have been washed from the fiber join that which originally passed through the screen 21 and advanced in the process. The next step is to separate the protein in as pure a form as possible, from this suspension of starch and protein.

The starch and gluten are separated using centrifugal machines 24 which produce a protein stream that contains from about 67 to 70% or even a little higher dry substance protein. This material is concentrated, filtered at 25 and dried in dryer 26 and sold as "corn gluten meal". It contains, in addition to protein and some 15 to 20% of starch a concentration of oils and fatty materials including "Xanthophyll oil" which is valued as a coloring material for use in chicken feed formulations. After the protein has been recovered, there remains a slurry of starch, with some protein, very fine fiber, and other materials in solution. The next step is to remove the protein fiber and solubles which is accomplished by countercurrent washing with fresh water in a series of stages of hydroclones 28, ranging in number from about 8 to 15 depending upon the specific conditions. The impure starch slurry 27 enters the first stage of the hydroclones and it leaves the last stage in a highly purified condition at a high concentration. This washed starch is then dried or used as the raw material for treated, converted, or blended starches, for dextrins, or sweeteners such as glucose, dextrose, high fructose syrup, etc.

Fresh water enters the last hydroclone stage and leaves the first carrying with it some starch as well as solubles, protein and fine fiber that have been washed from the product. The weight of dry material washed back at this point is often as much as 20 to 25% of the dry substance amount entering the washing station. It is concentrated in a centrifugal machine 29 and returned to the main stream 30 either before the fiber washing station or before the protein separator 24.

The outstanding features of this process are the recovery of high yields of starch and by-products in purified conditions that add to the value of each of them. Furthermore, this is accomplished with the use of small amounts of fresh water—in the order of 11 to 12 gallons or less per bushel (56 lbs) of corn ground, and no water leaves the process except as part of steepwater, starch slurry or dewatered by-products, and this is removed by evaporation or drying, or leaves as part of the product or by-product.

However, in order to achieve these results, there are certain penalties that must be paid: To free the maximum amount of starch during the steeping operation, some protein and carbohydrates are solubilized and become part of steepwater rather than the more valuable Gluten Meal or starch. To recover the maximum starch that is bound to the fiber, considerable power is used in milling, and undesirable amounts of very fine fiber, which are very difficult to remove, are formed. The recycle of the starch wash overflow results in accumulations of fine fiber, broken starch granules, and protein, which make gluten separation difficult.

It has been found that many of these problems can be overcome by adding a sub-process for alcohol production, whereby starch is recovered as alcohol from various of the streams. If the fibers are processed for alcohol, a great deal of power for milling may be saved, and less starch is carried to lower value Corn Gluten Feed; if part or all of the starch washing recycle mainstream is processed for alcohol recycle of extra fine fiber and broken starch granules is interrupted and gluten separation is improved. (The presence of variable alcohol capabilities has an added advantage of providing means to smooth out seasonal variations in demand for starch products.) When more alcohol is required than can be supplied from the starch in fiber and starch washing recycle, other streams, such as the flow 27 from the protein separator 24 to the starch washing station 28 can be tapped into as indicated by the valves 40,41,42 of FIG. 1.

Alcohol is produced from the starch in these streams in the same manner as if it were whole grain being processed as described above by cooking at 31, saccharifying 32, fermenting 33, distillation 34 to remove the alcohol and recovery at 35 of the unfermented materials. This latter step is different from whole grain processing in that the solubles content of the solution is very much lower, so it may be recycled in toto. The insoluble fraction 36 is also less since it has been reduced by the prior removal of the germ and part of the protein. After dewatering, the insolubles are mixed with concentrated steepwater from evaporator 13 and dried to produce animal feed material. However, this feed is higher in protein content than the Corn Gluten Feed of regular corn wet-milling due to (1) removal of starch which increases the percentage of protein, and (2) the protein in the starch washing recycle (and separator underflow when used) is recovered along with the fiber. Since the protein content of this feed material is higher than the normal product, it commands a higher price in the market. Alternatively, a standard protein content can be achieved by adding lower-cost materials, thus increasing the quantity produced.

Nevertheless, the quantity of more valuable Corn Gluten Meal is reduced by virtue of diversion of protein to less valuable feed.

Compared with the Prior Art distillery process, alcohol produced in this manner is very much less costly, basically due to the higher value of the up-graded by-products and to the use of much less water for which energy must be expended in evaporation and drying. The method also benefits from the economies of scale induced by combining with major starch producing facilities, especially when the quantity of alcohol is small in relation to the amount of corn processed.

However, when it is desired to produce large amounts of alcohol with relation to the starch produced, or when it is desired to make no starch at all, certain of the process steps become superfluous, and certain of the process advantages become diminished. The novel process described below and diagrammatically shown in FIG. 2 has been designed to not only overcome these difficulties but also to produce a new and valuable product.

Figure 2:
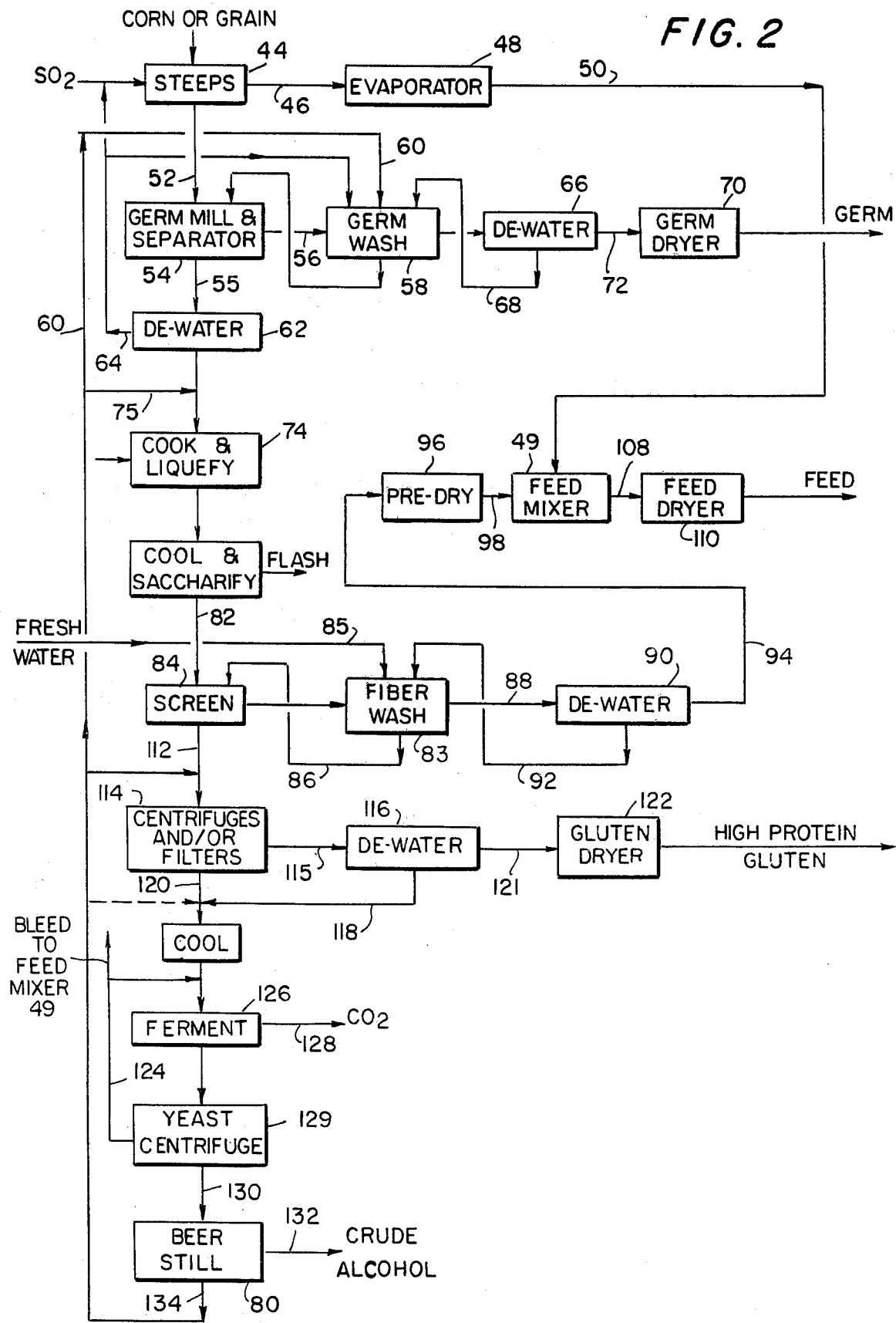
FIG. 2 is a flow sheet illustrating a preferred embodiment of the present invention.

As shown in FIG. 2, the first step of the process is to soak the corn for a length of time in warm water that has been acidified with sulfur dioxide at about 50° C. in tanks through which the water flows successively, as is standard practice in the corn wet-milling industry. The process differs from the standard procedure (where starch is sought as the prime product) in that steeping is carried out for a shorter period of time, only long enough to toughen the hull and germ sufficiently to make clean germ removal possible in the next step. Because of the shorter period of steeping, there is less solubilization of starch and protein, and therefore, a lower yield of steepwater solids than would be normal. The carbohydrates and proteins that would otherwise be solubilized are now available for recovery as alcohol and gluten respectively. Light steepwater exiting the system is kept preferably high in solids to reduce the amount of water needed to evaporate in the following evaporator. This is accomplished by balancing the amount of fresh water supplied the whole system.

The next step is that of germ removal which is carried out according to any standard corn wet-milling method which recovers germ with little adhered starch and protein, in a form suitable for expelling or extracting its valuable corn oil.

The magma remaining after steeping and germ removal is composed of water, solubles and insoluble material, with water comprising approximately 75 to 80% by weight of the total. The solubles are minerals, proteins, carbohydrates and other materials, while the insolubles consist primarily of starch, protein, fiber and fatty materials. Since the presence of high concentrations of solubles impedes the ability to recycle waters later in the process, it is important to reduce them as much as possible at this point, before the starch is cooked and solubilized.

This is accomplished by dewatering the magma to as low a moisture content as possible, and using the water to wash germ and especially to supply water to the steeps whence it exits as light steepwater. This is effective since solubles follow the water, and if the magma is dewatered from 80% moisture to 50% moisture, only one-fourth of the solubles will go forward with the dewatered material. Further reduction can be obtained by resuspending the material and dewatering it again. It is optional whether the material is milled further either before or after dewatering.

The next steps of the process are designed to convert all or essentially all of the starch to fermentable sugars, remove all or essentially all the carbohydrates and protein from the fiber, and to remove the fiber from the system; then to remove the protein from the system in a highly purified state. This is accomplished by the successive steps of (1) liquefying and saccharifying the starch, (2) screening out the fiber and washing it free of adhering materials by counter-current washing with water low in solubles, (3) removing the remaining insoluble material (primarily protein) by centrifugal or other means, followed by dewatering (with or without washing) and drying.

The remaining solution consists primarily of sugars which may be treated further to produce commercial useful sweeteners or they may be used as a substrate for fermentation to other materials of which ethanol is the most interesting use for fuel. The following descriptions enlarge upon the steps outlined above:

(1) The liquefaction and saccharification of the starch may be carried out by any of the methods normally used in the industry, such as the "acid", "acid-enzyme" or "enzyme" processes. In the acid conversion method, the starch slurry is cooked at an elevated temperature in the presence of strong acid, usually hydrochloric. The starch is converted into shorter-chain carbohydrates having a composition ranging from a high percentage of dextrin and starch-like compounds to a very high percentage of dextrose (D-Glucose), depending upon the conditions of treatment.

In the acid-enzme method, liquefaction and some saccharification are done with acid, followed by adjustment of conditions and saccharification with glucoamylase enzyme.

In the enzyme method, liquefaction is carried out with alpha-amylase and saccharification with glucoamylase or both may be done with mixed enzymes such as those in barley malt or certain fungal amylases.

(2) After the saccharification step, the carbohydrates may be easily washed from the fiber, carrying other solubles and finely divided insolubles, including the protein, with them. This is carried out by counter-current washing with fresh or other low-soluble water in a bent-screen or other fiber washing arrangement which is normally used in the starch industry, except that fewer stages are required to reduce the amount exiting with the fiber to a very low level.

After washing, the fiber is dewatered and may be dried separately or in combination with concentrated steepwater to produce Corn Gluten Feed, an item of commerce that is used as an ingredient in animal feeds. Other materials such as corn screenings, refinery residue, etc. may also be added to this feed as is normal practice in the industry. Water removed in the dewatering operation is passed to the fiber washing station and, by moving counter-currently, helps return the soluble carbohydrates to the main stream.

(3) The liquid remaining after removal of the washed fiber is a solution consisting of fermentable sugars and small amounts of other solubles such as inorganic salts and protein. Suspended in this are insoluble substances such as protein (primarily) with small amounts of finely divided fiber, and oils and fats.

These insoluble substances are removed by centrifugal methods which are common in the art, single stage or multiple; or by filtration alone or in combination with centrifugation, with or without counter-current washing. They are dried to about 10% moisture. Compared with the gluten produced by normal corn wet-milling, this product is very highly purified and contains up to 90% or more pure protein on a dry substance basis, as compared with normal 67 to 75%. It contains a concentration of the xanthophyll oil from corn, which is the coloring material that is used to bring yellow color to poultry skin and eggs via their feeds. This oil may be recovered by solvent extraction with hexane or other appropriate non-toxic solvent. Because of its extremely high protein content, the gluten has exceptional value as animal or human food and as a starting point for further processing.

(4) After removal of the insolubles, the solution consists essentially of sugars, which can be processed in different ways. The sugars can be concentrated by evaporation to form syrup with or without refining; cast as solid sugar or crystallized as dextrose, or they can be reacted chemically or especially fermented to various compounds, of which ethanol is of major importance.

To produce alcohol, the sugar solution is cooled to a suitable temperature for yeast fermentation in either batch or continuous processing. After fermentation is complete, yeast—both that which was introduced and that which grew during the course of the fermentation—is essentially the only insoluble material present. It can then be removed centrifugally, as is often done in molasses fermentations, but not previously practiced with grain, and reused in a fermentation vat. This recycle allows use of greater amounts of yeast resulting in faster fermentation. This recycling also obviates the need for growing more yeast from the sugars, thereby ensuring a higher yield of alcohol to the extent that the yeast multiplies due to partially aerobic conditions in the fermentation, there is excess yeast to be removed in the form of dead and damaged cells as well as good ones. Since these cells consist of high amounts of protein, they are useful as an additive to feed materials.

An example of the practice of the invention is given in the flow sheet of FIG. 2. A charge consisting of 1183 pounds (1000 pounds of dry substances) of clean corn is placed in a series of tanks 44 through which warm $SO_2$ water is flowed at 50° C. for steeping or leaching the corn for 10 to 30 hours. The yield of steepwater solids was 65 pounds and the light steepwater exiting through line 46 was found to total 813 pounds including 748 lbs. of water, 682 pounds of water were evaporated in multi-effect evaporator 48. The concentrated steepwater from evaporator 48 was flowed to feed mixer 49 via line 50.

The charge was flowed from tanks 44 via line 52 to germ mill and separator system 54 which includes a coarse attrition mill and hydrocyclones as is commonly practiced. The germ in the overflow were sent along line 56 for washing in washer 58 using recycled water introduced through line 60. Water is also recycled from dewatering station 62 via line 64 and from germ dewatering station 66 via line 68. The germ is dewatered in the presses of station 66 and sent on to germ dryer 70 by way of line 72. After drying, the recovered germ was found to be 79 pounds including 2% moisure and approximately 39 pounds of oil.

The underflow from separator system 54 containing fibers, starch, protein, soluble and insoluble materials is flowed to station 62 via line 55 where the water content thereof is dewatered from about 80 to about 50%. Optionally, the material is milled before dewatering. The expelled water is recycled to wash the germ and for steeping via line 64.

In this example, the enzyme method of liquefaction and saccharification was used. The dewatered material is flowed through the cooking and liquefying section 74 where the pH is adjusted, alpha-amylase such as Termamil 60 of Novo Industri A/S is added, with the addition of 313 lbs of water introduced by line 75 which recycles water from the bottom of the beer still.

Some 360 pounds of direct steam are injected during the cooking process, and 300 pounds are flashed off after cooking, during cooling to saccharification temperature of about 60° C., the pH is adjusted to 4.0 to 4.5 and enough glucoamylase is added to reach a dextrose equivalent of about 75 in about 6 hours. Using an enzyme such as Novo 150 produced by Novo Industri A/S the quantity is approximately 1 to 1.5 liters per metric ton of dry substance starch.

After saccharification of the starch, the stream passes through line 82 to screening section 84 for removal of coarse insoluble materials, almost entirely fiber. This is accomplished in a few stages of bent screens such as normally used in the industry.

The fiber is removed by a fine screen, and is then successively resuspended in counter-currently flowing water from tank 83 and rescreened to remove a maximum of the soluble material, in section 84. 1033 pounds of fresh water are introduced here via line 85 and is part of the counter-current washing stream. The solubles removed from the fiber pass through line 81 to the first screen in 84 and through it to the next station. Washed fiber passes through line 88 to a dewatering press 90 of usual type, where the moisture content is reduced mechanically from about 95% to 63%. Water removed here (1401 lbs.) returns to the washing station through line 92 while the dewatered fiber passes through line 94 to a pre-dryer 96 where the moisture content is reduced to approximately 20 to 40%. Predried fiber then passes through line 98 to feed mixer 49 where it is mixed with concentrated steepwater as well as other materials which may optionally be added here such as corn cleanings, refinery residue, etc. The mixture then passes through line 108 to Feed Dryer 110 where it is dried in normal fashion to approximately 10% moisture content with usual milling, screening and recycle.

The sugar solution, which still contains finely divided, suspended particles of insoluble protein, is sent on by line 112 to one or more centrifuges and/or filters 114 for removal of the protein (gluten). Prior to and during the process of protein recovery some 2422 pounds of water recycled from the bottom of the beer still 80 are added to the stream as a means of washing the protein and to dilute the sugars to the concentration required in the fermentation step. The 65 pounds of recovered protein is then dewatered in a filter 116 from approximately 88% moisture to about 60% moisture. The water removed at this step which contains sugars, is flowed in line 118 and passes through line 118 to join the sugar solution coming from filters 114 through line 120. The dewatered gluten is then flowed through pipe 121 and dried in a usual manner to about 10% moisture in dryer 122.

The sugar solution is then cooled to fermentation temperature of about 30° C. and recycled yeast is added through line 124. The amount of water here is adjusted to control the concentration of alcohol in the fermented mash as required by the amount and type of yeast employed, fermentation time available, and other pertinent variables. In the example an alcohol concentration of 8.1% by weight (about 10% by volume) was obtained.

Fermentation is carried out in station 126, which may be any sort of batch, semi-continuous or continuous process. During fermentation, some 398 pounds of carbon dioxide gas are evolved and this may be recovered or not according to the economics of the case.

After fermentation has been concluded, the mash passes through a normal type of nozzle centrifuge 129 for recovery of the yeast. Most of this is returned through line 124 to the fermenter station, but some is bled off and incorporated into the Corn Gluten Feed. The fermented mash, which is now essentially free of insolubles passes through line 130 to the first distillation stage 80 (often called "beer still") where the alcohol is stripped from the mash through line 132. In the example, 384 pounds of crude alcohol were recovered for further processing, at a concentration of about 74% by weight. This concentration may be varied according to usual practice, and the alcohol can be further processed as required to produce spirits for beverage, industrial, fuel, or other uses.

The water discharged from the bottom of the beer still 80 column contains very low solubles and is recycled through line 134 for re-use at earlier points in the process as described above.

Table I below provides a comparison between yields obtained with the present process and the prior art distillery process. In that table, it is noteworthy to remark that the present process uses only 682 pounds of fresh water against 3212 pounds by the prior art process. It also used 360 pounds of steam against 547 pounds by the prior art process. The amount of alcohol produced by the present process is 384 pounds against 369 pounds yielded by the other distillery process. Advantageously, the subject process produces corn oil and gluten not produced by the other.

| | Lbs/1000 lbs Clean Corn D.S. (Dry Solids) | |
|---|---|---|
| Production | Distillery | Present New Process |
| Alcohol (Absolute Basis) | 369 | 384 |
| Feed Product | | |
| 30% Protein | 362 | — |
| 21% Protein | — | 232 |
| Corn Oil | — | 34 |
| Gluten (80% Protein) | — | 72 |
| Fresh Water Consumed by Process | 3413 | 1033 |
| Steam for Cooking | 547 | 360 |
| Water to be Evaporated | | |
| in Dryers | 488 | 362 |
| in evaporators | 3212 | 682 |

The above example has been given as only one presently preferred embodiment of the invention. Many variations within its spirit will occur to those skilled in the art and these variations also form part of this invention.

For example, the advantages of this process may be combined with the starch alcohol process earlier described in FIG. 1.

It may also advantageously be combined with the classical distillery process where grain is dry-milled. The process may be shortened to remove both germ and fiber together.

The raw material used may be any carbohydrate bearing materials such as grain sorghum (milo), wheat, barley, rice, soybean, alfalfa, tapioca, potato, yams and bananas.

The sugars may be fermented to materials other than alcohol, such as N-butanol and acetone, glycerol, lactic acid, butylene glycol, citric, gluconic and itaconic acids and derivatized compounds thereof by reactions known per se.

The sugars may be removed without fermentation as a concentrated syrup, as cast or crystallized sugars.

The process may be practiced without recycle of the yeast, where its production is given preference over yields of alcohol.

The various non-carbohydrate streams may be combined in different ways with or without addition of other materials to form different by-products without departing from the spirit of the invention.

The process may be practiced without full recycle of the liquid remaining after the alcohol has been stripped off, without affecting the scope of the invention, but this will require more fresh water and energy to evaporate the liquid.

Another embodiment of the invention is its use in improving the traditional distillery process for producing alcohol where a dry-milled grain is used. In this process, the ground grain is suspended in water, and the starch converted to sugars by successive steps of cooking and treatment with acids and/or enzymes. The temperature and acidity are adjusted and the resulting mash is placed in a fermenter tank and 'starter' yeast is supplied from an outside source. In the fermenter tank, the yeast consumes the fermentable sugars and both propagates itself and produces alcohol. When the sugar has been consumed, the alcohol is removed by distillation, and the non-fermentable materials are recovered for use as an animal feed product, usually as a single by-product called "Distillers Dried Grains and Solubles".

This process may be improved in several ways by using the invention:

(1) Yeast may be recycled and this results in using shorter fermentation time and smaller fermenters.

(2) More alcohol is formed from the carbohydrate, since less yeast is grown.

(3) A new by-product which contains high purity protein is produced.

FIG. 3 outlines the traditional process, and FIG. 4, the application of the novel process. In the latter case, the coarse insolubles (mostly cellulosic materials), and the fine insolubles (mostly protein and fatty materials) are removed before fermentation. After fermentation, the yeast which is the only remaining insoluble material is recovered centrifugally and returned to the fermenters. Animal feed is produced by drying the coarse insoluble together with the solubles; no decanter is required after the stills, since the insolubles have already been removed in earlier steps.

What is claimed is:

1. A process for obtaining from carbohydrate-bearing grain high yields of soluble carbohydrates, a protein fraction essentially free of carbohydrates, and ethanol which comprises, in combination, the steps of:
   (a) steeping said grain in water for a period of time sufficient only to toughen the hull and germ thereof to facilitate subsequent separation and to form a steepwater;
   (b) separating said steepwater from said grain and concentrating said steepwater to produce feedstuff.
   (c) degerminating said grain and recovering germ containing oil and minimum amounts of starch and protein leaving a magma containing 75 to 80% by weight of water including minerals, proteins and carbohydrates and insolubles including starch, protein, fiber and fatty materials;
   (d) forming a slurry of said magma resulting from step (c) with water;
   (e) saccharifying the carbohydrates from said carbohydrate material to produce a sugar solution containing sugars, other water-soluble compounds and suspended coarse and fine insoluble materials;
   (f) removing the coarse insolubles from said sugar solution;
   (g) removing, washing and drying the fine insolubles comprising principally protein from said sugar solution;
   (h) cooling and adding yeast to said sugar solution and fermenting same to produce ethanol;
   (i) recovering at least a portion of said yeast from said fermented material in (h) and recycling same for further fermentation;
   (j) distilling ethanol from the fermented material;
   (k) recycling water remaining after distillation to said solution and to wash said protein.

2. The process of claim 1 in which the magma remaining after steeping and degerminating is dewatered to reduce the amount of solubles which move forward in the process and the water expelled is recycled to wash said germ and to steep said grain.

3. The process of claim 1, wherein coarse insoluble materials are washed to remove the carbohydrates therefrom, leaving a sugar solution in which finely divided particles of protein and other finely divided particles are suspended.

4. According to claim 3 wherein the fine insolubles are recovered from the sugar solution by filtration or centrifugation.

5. The process of claim 4, wherein after said sugar solution is freed of insoluble protein by filtration and/or centrifugation or other suitable means, said protein is separated from sugar solution, dewatered (and dried) from about 88% moisture to about 60% moisture and the extracted water is recycled to said sugar solution.

6. The process of claim 1, wherein said material is selected from the group of grain sorghum, wheat, barley, corn, rice, soybean, alfalfa, tapioca, potato, yams, and banana.

7. The process of claim 1, wherein said sugar solution is converted to n-butanol, acetone, glycerol, lactic acid, butylene glycol, citric acid, gluconic acid or itaconic acid.

8. A process according to claim 1, in which the carbohydrate material is dry milled, the dry milled material is slurred with water, the carbohydrates are converted to a solution containing sugars, other water soluble compounds and suspended insoluble materials removing therefrom a mash of coarse insolubles consisting mainly of cellulosic material; removing fine insolubles consisting mostly of protein and fatty materials from said mash; separating and recovering said protein; adding yeast to the remaining material to ferment same; centrifugally recovering said yeast; recycling said yeast for futther fermentation; distilling alcohol from said material.

9. The process of claim 1, wherein carbon dioxide produced during fermentation is recovered.

10. The process of claim 1, wherein said slurry is (1) separated from steepwater; (2) said steepwater is concentrated to yield material suitable as feedstuff; (3) said slurry is degermed; (4) said germ is recovered while (5) the remaining underflow containing fibers, starch, protein, soluble and insoluble materials is dewatered from about 80 to 50% water; (6) said underflow then being cooked; (7) cooled to saccharification temperature; (8) its pH adjusted to 4.0 to 4.5 and (9) from 1 to 1.5 liters of amylase per ton of dry starch is added.

11. The process of claim 10, wherein said fibers are removed dewatered, pre-dried to a moisture content of 20 to 40%, mixed with said concentrated steepwater and the resulting mixture is dried to form feedstuff.

12. The process of claim 1, wherein said sugar solution is concentrated to form syrup, cast as solid sugar or crystallized as dextrose.

13. The process of claim 1, wherein said grain is corn and said steeping lasts ten to thirty hours.

* * * * *